(12) United States Patent
Burns (10) Patent No.: US 9,433,373 B2
(45) Date of Patent: Sep. 6, 2016

(54) METHOD AND APPARATUS FOR MATHEMATICALLY CHARACTERIZING EAR CANAL GEOMETRY

(75) Inventor: Thomas Howard Burns, St. Louis Park, MN (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 938 days.

(21) Appl. No.: 12/793,784

(22) Filed: Jun. 4, 2010

(65) Prior Publication Data

US 2010/0312533 A1  Dec. 9, 2010

Related U.S. Application Data

(60) Provisional application No. 61/184,402, filed on Jun. 5, 2009.

(51) Int. Cl.
*G06F 17/10* (2006.01)
*A61B 5/107* (2006.01)

(52) U.S. Cl.
CPC .................. *A61B 5/1076* (2013.01)

(58) Field of Classification Search
CPC .................................... A61B 5/1076
USPC .......................................... 703/2
See application file for complete search history.

(56) References Cited

U.S. PATENT DOCUMENTS

| | | | |
|---|---|---|---|
| 4,190,033 A | 2/1980 | Foti | |
| 5,190,046 A | 3/1993 | Shturman | |
| 5,735,282 A * | 4/1998 | Hossack | 600/458 |
| 6,093,150 A * | 7/2000 | Chandler et al. | 600/459 |
| 6,631,197 B1 | 10/2003 | Taenzer | |
| 6,751,494 B2 * | 6/2004 | Collier et al. | 600/407 |
| 7,175,599 B2 | 2/2007 | Hynynen et al. | |
| 7,878,977 B2 * | 2/2011 | Mo et al. | 600/459 |

(Continued)

FOREIGN PATENT DOCUMENTS

| | | |
|---|---|---|
| DE | 4135286 C1 | 1/1993 |
| GB | 2344555 A | 6/2000 |
| WO | WO-0034739 A2 | 6/2000 |

OTHER PUBLICATIONS

John A. Hossack et al., "Improving the characteristics of a transducer using multiple active layers," 1993, IEEE Transactions on Ultrasonics, Ferroelectrics, and Frequency Control, vol. 40, No. 2, pp. 131-139.*

(Continued)

*Primary Examiner* — Kamini S Shah
*Assistant Examiner* — Russ Guill
(74) *Attorney, Agent, or Firm* — Schwegman Lundberg & Woessner, P.A.

(57) ABSTRACT

The present subject matter provides apparatus and methods for physically fitting a hearing assistance device, including mathematically characterizing a person's ear canal. The apparatus includes a housing adapted to be mechanically coupled to the person in proximity to the person's outer ear. An ultrasonic transducer array is located within at least a portion of the housing. The apparatus includes electronics within the housing, the electronics adapted to control the transducer array to alternate between transmitting and receiving ultrasonic energy. In various embodiments, a processor is adapted to characterize geometry of the ear canal using information from the ultrasonic transducer array obtained from scans of the ear canal.

20 Claims, 7 Drawing Sheets

(56) References Cited

U.S. PATENT DOCUMENTS

| | | |
|---|---|---|
| 7,998,073 B2* | 8/2011 | Roth et al. ............ 600/437 |
| RE42,803 E * | 10/2011 | Lipson et al. ............ 600/454 |
| 8,840,558 B2 | 9/2014 | Burns |
| 2001/0020126 A1 | 9/2001 | Swanson et al. |
| 2002/0050518 A1* | 5/2002 | Roustaei ............ 235/454 |
| 2003/0051323 A1* | 3/2003 | Gururaja ............ 29/25.35 |
| 2004/0049110 A1* | 3/2004 | Cai et al. ............ 600/437 |
| 2004/0107080 A1* | 6/2004 | Deichmann ............ A61F 11/08 703/6 |
| 2004/0181128 A1* | 9/2004 | Masters ............ G01B 11/24 600/200 |
| 2004/0202990 A1* | 10/2004 | Geiger ............ 434/262 |
| 2004/0204650 A1 | 10/2004 | Taylor |
| 2004/0210135 A1* | 10/2004 | Hynynen et al. ............ 600/439 |
| 2004/0221853 A1 | 11/2004 | Miller |
| 2005/0018540 A1* | 1/2005 | Gilbert et al. ............ 367/138 |
| 2005/0027251 A1 | 2/2005 | Masters |
| 2005/0065426 A1 | 3/2005 | Porat et al. |
| 2005/0251035 A1* | 11/2005 | Wong et al. ............ 600/437 |
| 2007/0016055 A1* | 1/2007 | Cao et al. ............ 600/459 |
| 2007/0016072 A1* | 1/2007 | Grunwald et al. ............ 600/468 |
| 2007/0027392 A1* | 2/2007 | Schwartz ............ 600/443 |
| 2007/0071266 A1* | 3/2007 | Little et al. ............ 381/328 |
| 2007/0075997 A1 | 4/2007 | Rohaly et al. |
| 2007/0127756 A1* | 6/2007 | Slabaugh ............ H04R 25/652 381/328 |
| 2007/0232910 A1* | 10/2007 | Hwang et al. ............ 600/437 |
| 2007/0276252 A1* | 11/2007 | Kolasa et al. ............ 600/459 |
| 2008/0199829 A1 | 8/2008 | Paley et al. |
| 2008/0229832 A1* | 9/2008 | Huang et al. ............ 73/620 |
| 2009/0036780 A1* | 2/2009 | Abraham ............ 600/459 |
| 2009/0306517 A1 | 12/2009 | Burns |
| 2012/0016243 A1* | 1/2012 | Brown et al. ............ 600/462 |

OTHER PUBLICATIONS

H. Taunaumang et al., "Electromechanical properties of 1-3 piezoelectric ceramic/piezoelectric polymer composites," 1994, Journal of Applied Physics, vol. 76, No. 1, pp. 484-489.*

Qian Zhang et al., "PVDF Transducers—A Performance Comparison of Single-Layer and Multi-layer Structures," 1997, IEEE Transactions on Ultrasonics, Ferroelectrics, and Frequency Control, vol. 44, No. 5, pp. 1148-1156.*

Rahul S. Singh et al., "Simulation, fabrication, and characterization of a novel flexible, conformal ultrasound transducer array," 2007, 2007 IEEE Ultrasonics Symposium, pp. 1824-1827.*

Pai-Chi Li et al., "Phase aberration correction on two-dimensional conformal arrays," 1995, IEEE Transactions on Ultrasonics, Ferroelectrics, and Frequency Control, vol. 42, No. 1, pp. 73-82.*

A.M. Dickie et al., "Ultrasound imaging of the canine tympanic bulla," 2003, Research in Veterinary Science, vol. 75, pp. 121-126.*

R. Greff et al., "Circumaural transducer arrays for binaural synthesis," Jun. 29, 2008, Acoustics'08, 9e Congres Franscais d'acoustique of the SFA, pp. 3878-3882.*

E.A.G. Shaw, "Hearing threshold and ear-canal pressure levels with varying acoustic field," 1969, The Journal of the Acoustical Society of America, vol. 46, No. 6 (part 2), pp. 1502-1514.*

"Harmonic Imaging," 1997, General Electric Company, six pages.*

"U.S. Appl. No. 12/478,200 , Response filed Jan. 13, 2012 to Non Final Office Action mailed Oct. 13, 2011", 8 pgs.

"U.S. Appl. No. 12/478,200, Non Final Office Action mailed Oct. 13, 2011", 14 pgs.

"European Application Serial No. 10251037.7, Extended European Search Report mailed Oct. 4, 2010", 5 pgs.

"European Application Serial No. 10251037.7, Response filed Jun. 7, 2011 to Extended European Search Report mailed Oct. 4, 2010", 7 pgs.

"U.S. Appl. No. 12/478,200 , Response filed Jan. 7, 2014 to Non Final Office Action mailed Oct. 7, 2013", 8 pgs.

"U.S. Appl. No. 12/478,200, Final Office Action mailed Feb. 27, 2014", 13 pgs.

"U.S. Appl. No. 12/478,200, Non Final Office Action mailed Oct. 7, 2013", 10 pgs.

"U.S. Appl. No. 12/478,200, Notice of Allowance mailed May 23, 2014", 8 pgs.

"U.S. Appl. No. 12/478,200, Response filed Apr. 28, 2014 to Final Office Action mailed Feb. 27, 2014", 8 pgs.

* cited by examiner

METHOD AND APPARATUS FOR MATHEMATICALLY CHARACTERIZING EAR CANAL GEOMETRY

CLAIM OF PRIORITY

The present application claims the benefit under 35 U.S.C. 119(e) of U.S. Provisional Patent Application Ser. No. 61/184,402, filed Jun. 5, 2009, which is hereby incorporated by reference in its entirety.

TECHNICAL FIELD

The present application relates to physically fitting hearing assistance devices, and in particular to mathematically characterizing ear canal geometry for physically fitting hearing assistance devices.

BACKGROUND

Modern techniques used by hearing instrument manufacturers for obtaining a person's ear canal geometry utilize highly-compliant polymeric materials that are injected into the canal with a syringe. After the material cures, it is pulled from the ear thereby giving a three dimensional impression of the ear canal geometry. Traditionally, the impression is cast in a silicone investment and removed, thereby leaving a representation of the original ear canal. In a procedure that is similar to the traditional casting of a bell, a custom earmold is created by pouring resins into the investment and allowing them to cure into plastic. Although this technique gives a reasonably accurate representation of the ear canal geometry, it does not yield any mathematical information about its shape.

Most hearing instrument manufacturers have adopted laser scanning of traditional impressions as the method of obtaining mathematical representations of the ear canal geometry. A dispenser will acquire the impression from the patient and mail the impression directly to the manufacturer. Unfortunately, the impression can become distorted during the mailing process due to uncured material and excessive temperatures in the delivery trucks; the result is an inaccurate impression of the patient's physiology thereby leading to a hearing instrument that does not fit properly. It is common practice for the dispenser to acquire another impression from the patient and return the hearing instrument for rework.

In some instances, it is common for the hearing instrument to pop out of the patient's ear during chewing or other jaw motion. Since the impression is obtained in a "static" condition within the ear canal, geometry changes of the ear canal during chewing can cause the hearing instrument to jostle and pop out. In order to mitigate these occurrences, it may be advantageous to acquire two different impressions: one with the jaw closed and one with the jaw open. The final earmold for the hearing instrument can be extrapolated as an average from the two impressions, thereby reducing the potential for "popout".

Depending on the cure rate of the polymeric material used for ear impressions, the process can typically take from ten to fifteen minutes per pair of impressions, not to mention administrative time in preparing, shipping, and receiving the impressions. Recently, laser technology has been used to scan the features of the impression into a mathematical format such as "point cloud" data. These data are used to create a custom shell with automated, digital shell making processes. Unfortunately, the inconvenience of taking a person's ear impression remains the first step in this procedure.

There is a need in the art for a better way to characterize the geometry of a person's ear canal. It would be advantageous to have a process that acquires a representation of the geometry of the ear canal in less time. It would be further advantageous to be able to forward data of the representation directly to a manufacturer to save shipping time and cost.

SUMMARY

The present subject matter provides apparatus and methods for physically fitting a hearing assistance device, including mathematically characterizing a person's ear canal. The apparatus includes a housing adapted to be mechanically coupled to the person in proximity to the person's outer ear. In various approaches, an ultrasonic transducer array is located within at least a portion of the housing. The apparatus includes electronics within the housing in various approaches, the electronics adapted to control the transducer array to alternate between transmitting and receiving ultrasonic energy. In various approaches, the apparatus includes a processor adapted to characterize geometry of the ear canal using information from the ultrasonic transducer array obtained from scans of the ear canal.

Various embodiments include a method for mathematically modeling a person's ear canal. The method includes mechanically coupling an ultrasonic transducer system in proximity to the person's outer ear. The ear canal is scanned using the ultrasonic transducer system, and a representation of geometry of the ear canal is obtained using information from the ultrasonic transducer system, in various approaches.

This summary is an overview of some of the teachings of the present application and is not intended to be an exclusive or exhaustive treatment of the present subject matter. Further details about the present subject matter are found in the detailed description and the appended claims. The scope of the present invention is defined by the appended claims and their equivalents.

DETAILED DESCRIPTION

The following detailed description of the present invention refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is, therefore, not to be taken in a limiting sense, and the scope is defined only by the appended claims, along with the full scope of legal equivalents to which such claims are entitled.

In various embodiments, the present subject matter provides an ultrasonic transducer system for the purpose of imaging the physiology of the ear canal, a housing to hold the transducer system and mechanically couple it to the skin at a position outside the skull and closely surrounding the pinna, electronics to operate the transducers in pulse-echo (B-mode) so that they can alternate between transmitting and receiving ultrasonic energy, and a signal processing scheme that utilizes the signals from the transducer array in order to mathematically characterize the ear canal geometry using signal processing algorithms. The mathematical representation would be valuable for an automated, digital shell making procedure such as stereo lithography. Such a process may be performed at a dispenser's office, and may facilitate use of the internet to send data directly to a manufacturer.

In an effort to preclude the need to "shoot" a person's impression with a syringe of polymeric material, at least one approach has been proposed that uses ultrasonic and/or optical devices located on the end of a straight, hand-held wand. The wand is inserted into the ear canal, and the device scans the geometry. If the device is based on an ultrasonic scanner, the ear canal must be filled with fluid thereby making the process inconvenient, messy, and impractical. If the device is based on an optical scanner, complicated mirrors and positioning devices are needed to rotate and control the optical light beam. If the beam is scattered by hair within the ear canal, imaging precision is degraded. In addition, getting useful information beyond the first bend of the ear canal is difficult with a straight wand, primarily because the wand presses against the skin and deforms the geometry it is trying to scan. To date, mass-produced scanning systems based on the ideas in this paragraph have not been successfully fabricated for the hearing instrument industry.

Thus, the present subject matter proposes an innovative approach to obtaining a geometrical representation of a person's ear canal. Medical ultrasonography is a highly refined procedure for bioimaging. In particular, transcranial ultrasonography is an area of medical ultrasonography that has recently developed into a useful imaging alternative to Computer Axial Tomography (CAT) scanning of a person's skull. The technological advances in transcranial ultrasonography as used in medical diagnostic imaging can be adapted to be used in a method and apparatus for mathematically characterizing ear canal geometry in an efficient solution for direct ear scanning.

In one embodiment, an ultrasonic transducer array is contained within a housing apparatus. The purpose of the housing apparatus, which can have variety of shapes, is to position the ultrasonic transducer array in a region on a person's skull, directly outside of and surrounding the outer ear. A number of configurations for the transducer array in the housing may be employed, including, but not limited to, those shown in FIGS. 1-7, according to various embodiments of the present subject matter. As such, the housing can have a circular, oval, square, rectangular, or rounded rectangular shape, as shown generally in FIGS. 1 thru 7.

Figure 1:
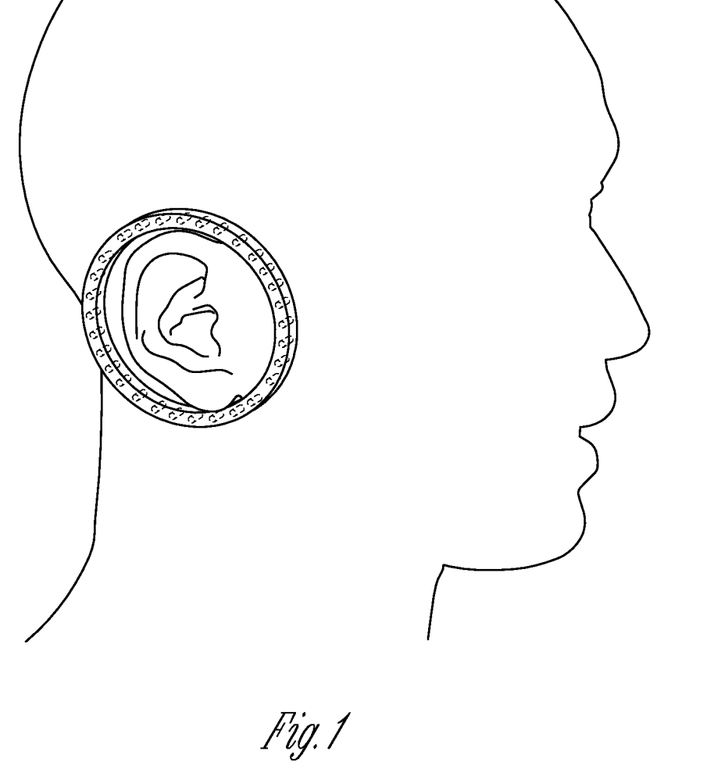
FIG. 1 illustrates a circular housing with an ultrasonic transducer array, according to one embodiment of the present subject matter.
Figure 2:
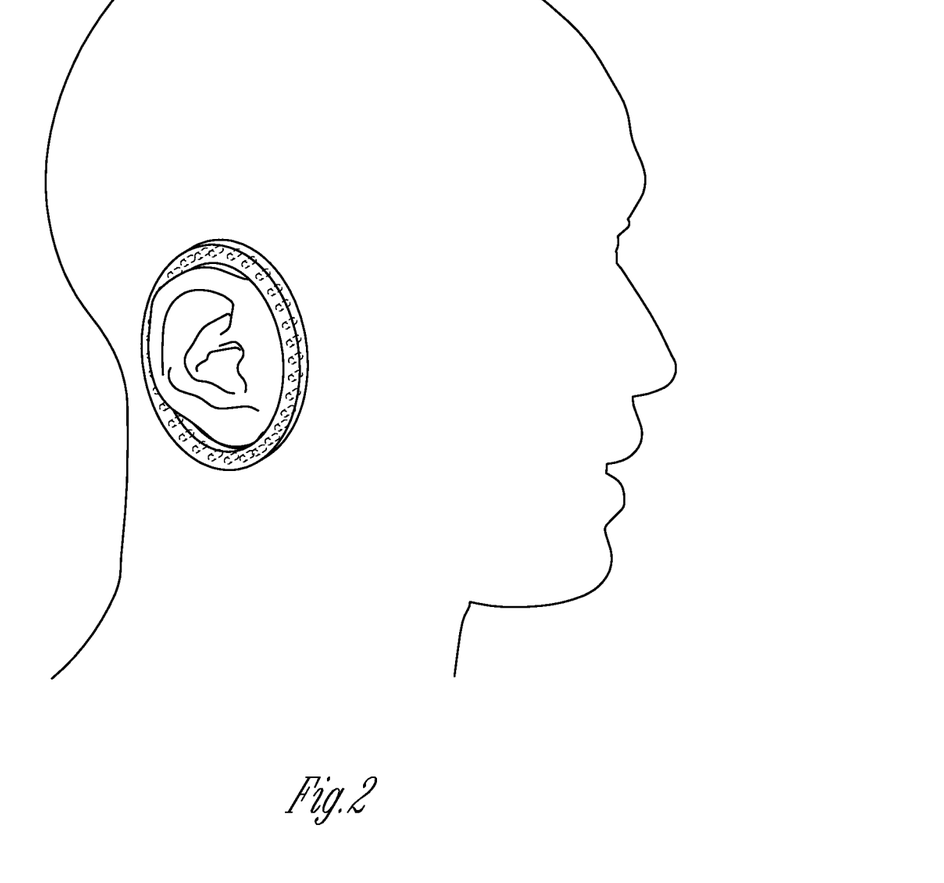
FIG. 2 illustrates an oval housing with an ultrasonic transducer array, according to one embodiment of the present subject matter.
Figure 3:
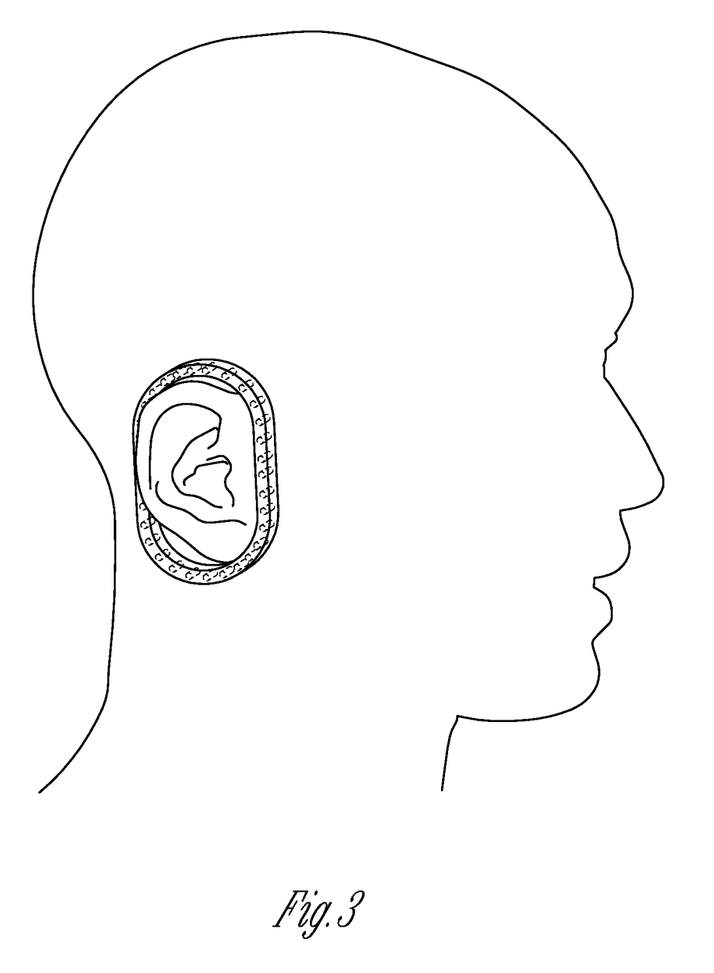
FIG. 3 illustrates a rounded rectangular housing with an ultrasonic transducer array, according to one embodiment of the present subject matter.
Figure 4:
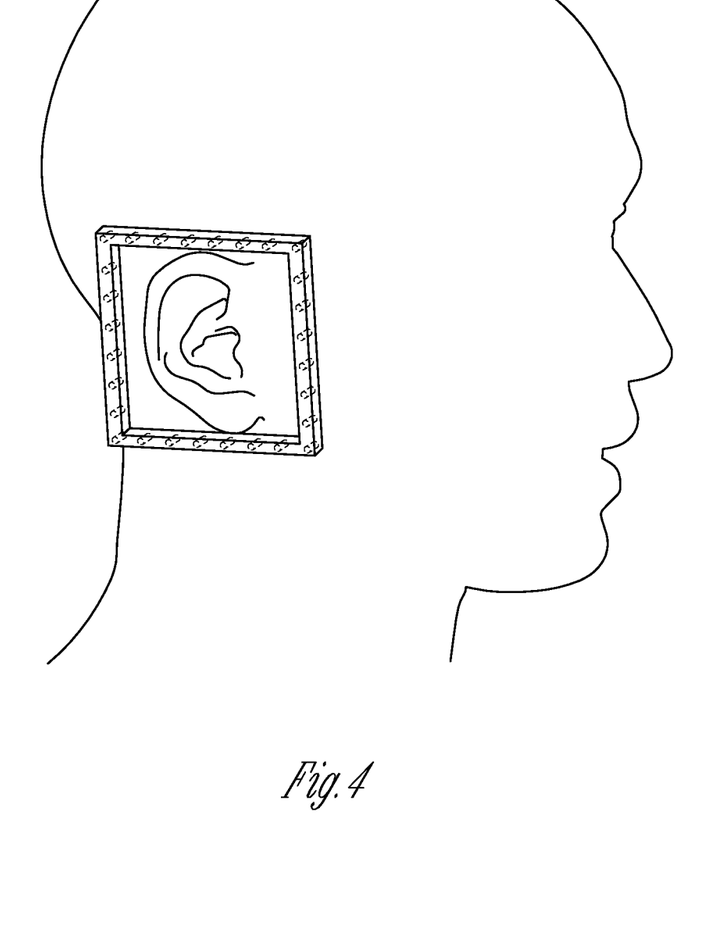
FIG. 4 illustrates a square housing with an ultrasonic transducer array, according to one embodiment of the present subject matter.
Figure 5:
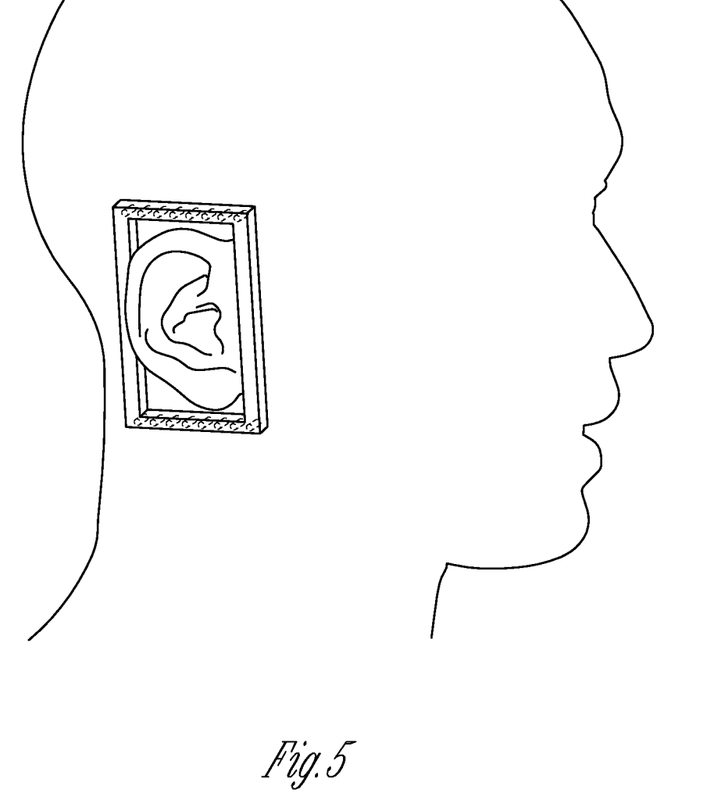
FIG. 5 illustrates a rectangular housing with a horizontal, collinear, ultrasonic transducer array, according to one embodiment of the present subject matter.
Figure 6:
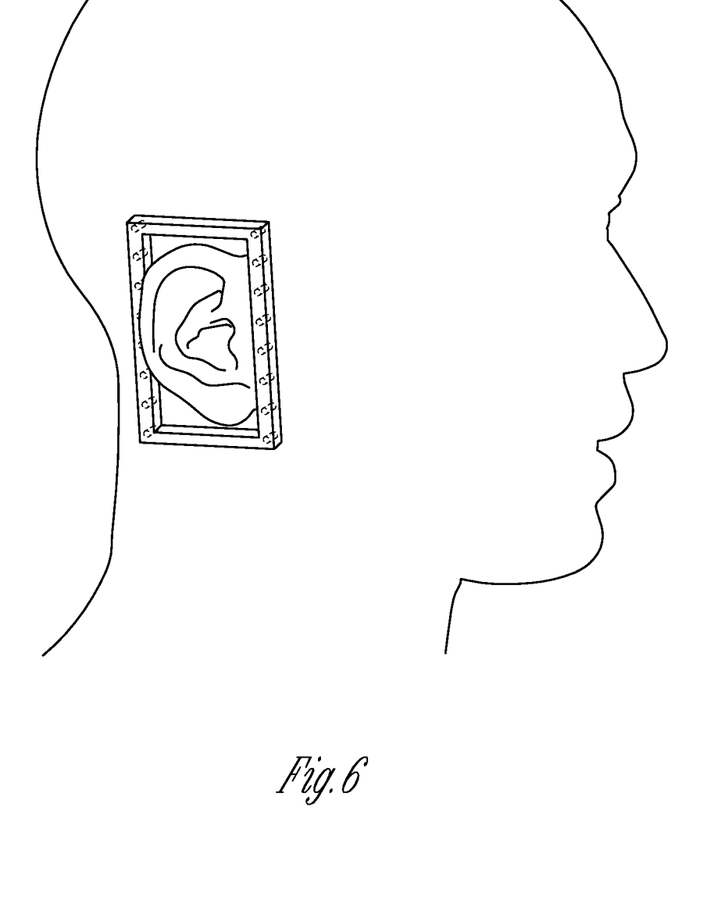
FIG. 6 illustrates a rectangular housing with a vertical, collinear, ultrasonic transducer array, according to one embodiment of the present subject matter.
Figure 7:
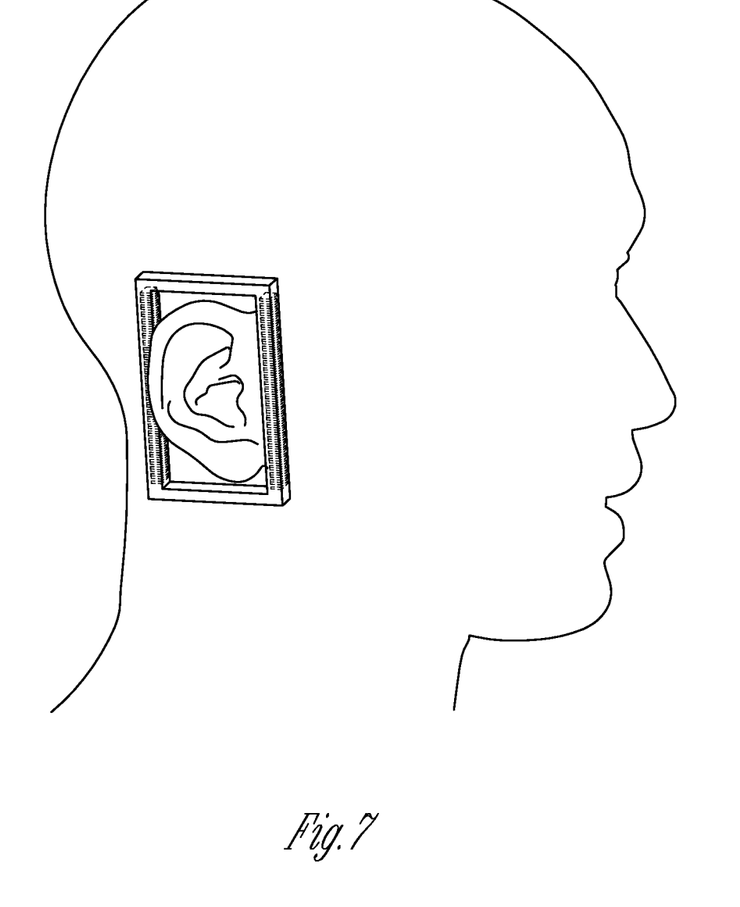
FIG. 7 illustrates a rectangular housing with a vertical, collinear, ultrasonic transducer array, according to one embodiment of the present subject matter.

The ultrasonic transducer array is comprised of multiple ultrasonic transducers. Each transducer can be fabricated from a piezoceramic or piezocrystal material. The operating range of frequencies for the transducer array includes, but is not limited to, about 1 MHz to 18 MHz. In one embodiment, the operating range is about 3 MHz to 12 MHz. In various embodiments, the operating range depends on one or more of at least: the depth of the ear canal, the desired spatial resolution of the scanned bioimage, and the allowable transmitted ultrasonic power. Each transducer, in general, can be fabricated from piezopolymer cylinders operating with 1-3 connectivity, or a piezopolymer matrix composite operating with 2-2 connectivity as depicted in FIG. 7.

The transducers in the ultrasonic transducer array operate as transceivers in pulse-echo mode. For example, the transducer transmits ultrasonic vibrations while simultaneously receiving ultrasonic energy. The process of transmitting and receiving can be executed in a narrow frequency band, in which case the transducer transmits, turns off, and then receives, or can be executed over a broad frequency range in which case the transducer transmits at, for example, a lower frequency region while simultaneously receiving the harmonics at a higher frequency region. In either case, the supporting electronics use the proper characteristics for filtering and time gating. This data acquisition technique could be expanded to use one transducer to transmit actively while every other transducer receives passively. If the transducer array contains, for example, 64 transducers, the active transducer could be switched from 1 to 64; in each switch, the remaining 63 transducers are passive. Thus, there exists the ability to acquire large data sets systematically. These empirical data are used in the numerical computations for the non-homogeneous integral equation formulations for elastic scattering. These integral equations could be solved by a variety of methods, including model-based processing, wave-based inversion, singular value decomposition, or other techniques that have been applied in applications such as biomedical vibroacoustography, geophysical prospecting, or any acoustical inverse boundary value problem.

Various embodiments include an apparatus for mathematically modeling a person's ear canal. The apparatus includes a housing adapted to be mechanically coupled to the person in proximity to the person's outer ear. In various approaches, an ultrasonic transducer array is located within at least a portion of the housing. The apparatus includes electronics within the housing in various approaches, the electronics adapted to control the transducer array to alternate between transmitting and receiving ultrasonic energy. In various approaches, the apparatus includes a processor adapted to characterize geometry of the ear canal using information from the ultrasonic transducer array obtained from scans of the ear canal. According to various embodiments, the processor is located within the housing. As used herein, a processor includes but is not limited to, a digital signal processor (DSP), a microprocessor, a microcontroller, or any other processing hardware. The processor is located remote from the housing, in various embodiments. The electronics are adapted to operate transducers in the transducer array in pulse-echo mode, in an embodiment. In various embodiments, the transducer array is adapted to operate in a range of frequencies from approximately 1 MHz to approximately 18 MHz. The transducer array is adapted to operate in a range of frequencies from approximately 3 MHz to approximately 12 MHz, in an embodiment. The transducer array can include multiple piezoceramic transducers, multiple piezocrystal transducers, transducers fabricated from piezopolymer cylinders operating with 1-3 connectivity, transducers fabricated from a piezopolymer matrix operating with 2-2 connectivity, a combination, or various other ultrasonic transducers, in various embodiments. According to various embodiments, the housing can have a circular shape, an oval shape, a square shape, a rectangular shape, a rounded rectangular shape, or other appropriate shape without departing from the scope of this disclosure.

Various embodiments include a method for mathematically modeling a person's ear canal. The method includes mechanically coupling an ultrasonic transducer system in proximity to the person's outer ear. The ear canal is scanned using the ultrasonic transducer system, and a representation of geometry of the ear canal is obtained using information from the ultrasonic transducer system. According to various embodiments, scanning the ear canal includes using transducers in pulse-echo mode. The method further includes, in various embodiments, sending the representation of the geometry of the ear canal to a hearing instrument manufacturer. Sending the representation includes sending data using the internet, in an embodiment. In various embodiments, the method also includes manufacturing a hearing instrument shell utilizing the representation of the geometry of the ear canal in a digital shell making procedure, such as stereo lithography. Other digital shell making procedure can be used without departing from the scope of this disclosure.

The present subject matter includes hearing assistance devices (or hearing instruments), including but not limited to, cochlear implant type hearing devices, hearing aids, such as behind-the-ear (BTE), in-the-ear (ITE), in-the-canal (ITC), or completely-in-the-canal (CIC) type hearing aids. It is understood that behind-the-ear type hearing aids may include devices that reside substantially behind the ear or over the ear. Such devices may include hearing aids with receivers associated with the electronics portion of the behind-the-ear device, or hearing aids of the type having receivers in the ear canal of the user. It is understood that other hearing assistance devices not expressly stated herein may fall within the scope of the present subject matter.

This application is intended to cover adaptations or variations of the present subject matter. It is to be understood that the above description is intended to be illustrative, and not restrictive. The scope of the present subject matter should be determined with reference to the appended claims, along with the full scope of legal equivalents to which such claims are entitled.

What is claimed is:

1. An apparatus for mathematically modeling a person's ear canal, the apparatus comprising:
    a housing including an aperture;
    an ultrasonic transducer array located within at least a portion of the housing, the housing adapted to position the ultrasonic transducer array on a person's skull outside of and surrounding a pinna, such that at least a portion of the pinna is within the aperture;
    electronics within the housing, the electronics adapted to control the transducer array to transmit ultrasonic energy at a first frequency and receive ultrasonic energy at a second frequency, wherein the second frequency is different than the first frequency, wherein the transducer array is configured for a frequency operating range dependent on a measured depth of the ear canal, wherein the depth of the ear canal is measured at least in part using the ultrasonic transducer array; and
    a processor within the housing, the processor configured to control each transducer in the transducer array and adapted to mathematically characterize geometry of the ear canal using information from the ultrasonic transducer array obtained from scans of the ear canal, wherein the mathematically characterized geometry of the ear canal is generated to create specifications for producing a hearing aid shell customized for at least a portion of the ear canal.

2. The apparatus of claim 1, wherein the processor includes a digital signal processor (DSP).

3. The apparatus of claim 1, wherein the electronics are adapted to operate transducers in the transducer array in pulse-echo mode.

4. The apparatus of claim 1, wherein the transducer array is adapted to operate in a range of frequencies from 1 MHz to 18 MHz.

5. The apparatus of claim 1, wherein the transducer array is adapted to operate in a range of frequencies from 3 MHz to 12 MHz.

6. The apparatus of claim 1, wherein the transducer array includes multiple piezoceramic transducers.

7. The apparatus of claim 1, wherein the transducer array includes multiple piezocrystal transducers.

8. The apparatus of claim 1, wherein the transducer array includes transducers fabricated from piezopolymer cylinders operating with 1-3 connectivity.

9. The apparatus of claim 1, wherein the transducer array includes transducers fabricated from a piezopolymer matrix operating with 2-2 connectivity.

10. The apparatus of claim 1, wherein at least one surface of the housing has a circular shape.

11. The apparatus of claim 1, wherein at least one surface of the housing has an oval shape.

12. The apparatus of claim 1, wherein at least one surface of the housing has a square shape.

13. The apparatus of claim 1, wherein at least one surface of the housing has a rectangular shape.

14. The apparatus of claim 1, wherein at least one surface of the housing has a rounded rectangular shape.

15. A method for mathematically modeling a person's ear canal, the method comprising:
    positioning an ultrasonic transducer system on a person's skull outside of and surrounding a pinna, wherein the ultrasonic transducer system includes an ultrasonic transducer array within a housing having an aperture, and wherein the positioning includes placing the housing such that at least a portion of the pinna is within the aperture;
    scanning the ear canal using the ultrasonic transducer system, including transmitting ultrasonic energy at a first frequency and receiving ultrasonic energy at a second frequency, wherein the second frequency is different than the first frequency, wherein the transducer array is configured for a frequency operating range dependent on a measured depth of the ear canal, wherein the depth of the ear canal is measured at least in part using the ultrasonic transducer array; and
    using a processor within the housing and configured to control each transducer in the transducer array to process information from the ultrasonic transducer system to obtain a representation of geometry of the ear canal, wherein the representation of geometry of the ear canal is generated to create specifications for producing a hearing aid shell customized for at least a portion of the ear canal.

16. The method of claim 15, wherein scanning the ear canal includes using transducers in pulse-echo mode.

17. The method of claim 15, further comprising:
sending the representation of the geometry of the ear canal to a hearing instrument manufacturer.

18. The method of claim 17, wherein sending the representation includes sending data using internet.

19. The method of claim 17, further comprising:
manufacturing a hearing instrument shell utilizing the representation of the geometry of the ear canal in a digital shell making procedure.

20. The method of claim 19, wherein the digital shell making procedure includes stereo lithography.

* * * * *